(12) United States Patent
Moumene et al.

(10) Patent No.: US 6,569,201 B2
(45) Date of Patent: May 27, 2003

(54) HYBRID COMPOSITE INTERBODY FUSION DEVICE

(75) Inventors: Missoum Moumene, Newton, MA (US); Hassan Serhan, South Easton, MA (US)

(73) Assignee: Depuy Acromed, Inc., Raynham, MA (US)

( * ) Notice: Subject to any disclaimer, the term of this patent is extended or adjusted under 35 U.S.C. 154(b) by 0 days.

(21) Appl. No.: 09/967,290

(22) Filed: Sep. 28, 2001

(65) Prior Publication Data

US 2003/0065393 A1 Apr. 3, 2003

(51) Int. Cl.⁷ .................................................. A61F 2/44
(52) U.S. Cl. ................. 623/17.11; 623/17.16; 606/61
(58) Field of Search ........................ 606/71, 61; 623/17

(56) References Cited

U.S. PATENT DOCUMENTS

| | | | |
|---|---|---|---|
| 4,834,757 A | * 5/1989 | Brantigan | ................. 623/17.11 |
| 4,863,477 A | 9/1989 | Monson | |
| 5,013,315 A | * 5/1991 | Barrows | ....................... 606/71 |
| 5,071,437 A | 12/1991 | Steffee | |
| 5,370,697 A | 12/1994 | Baumgartner | |
| 5,425,772 A | 6/1995 | Brantigan | |
| 5,458,653 A | 10/1995 | Davidson | |
| 5,514,180 A | 5/1996 | Heggeness et al. | |
| 5,534,030 A | 7/1996 | Navarro et al. | |
| 5,702,450 A | 12/1997 | Bisserie | |
| 6,039,762 A | 3/2000 | McKay | |
| 6,126,688 A | 10/2000 | McDonnell | |
| 6,146,420 A | 11/2000 | McKay | |
| 6,241,734 B1 | 6/2001 | Scribner et al. | |
| 6,241,771 B1 | 6/2001 | Gresser et al. | |

OTHER PUBLICATIONS

Kandziora, F., TGF–b and IGF–I Application by a Poly–(D, L)–lactide coated interbody cage promotes fusion in the sheep cervical spine . . . 47ᵗʰ Annual Meeting, Orthopaedic Research Society, Feb. 25–28, 2001, San Francisco, CA.*

Bradley K. Weiner, M.D. and Robert D. Fraser, M.D., "Spinal Update Lumbar Interbody Cages", *SPINE*, vol. 23, No. 5, pp 634–640, 1998.

Kandziora, F., TGF–b and IGF–I Application by a Poly (D,L)–Lactide Coated Interbody Cage Promotes Fusion in the Sheep Cervical Spine; Radiographic and Biomechanical Results—47ᵗʰ Annual Meeting, Orthopaedic Research Society, Feb. 25–28, 2001, San Francisco, California.

G. Schmidmaier, "Biodegradable Poly (D,L–Lactide) Coating of Implants for Continuous Release of Growth Factors", J Biomed Mater Res (Appl Biomater) 58: 449–455, 2001.

* cited by examiner

*Primary Examiner*—David J. Isabella
*Assistant Examiner*—Kamrin Landrem
(74) *Attorney, Agent, or Firm*—Tom DiMauro (57) ABSTRACT

A fusion cage having a structural bioresorbable layer thereon.

41 Claims, 13 Drawing Sheets

HYBRID COMPOSITE INTERBODY FUSION DEVICE

BACKGROUND OF THE INVENTION

The leading cause of low back pain arises from rupture or degeneration of lumbar intervertebral discs. Pain in the lower extremities is caused by the compression of spinal nerve roots by damaged discs between the vertebrae, and low back pain is caused by collapse of the disc and by the adverse effects of bearing weight through a damaged unstable vertebral joint. One conventional method of managing this problem is to remove the problematic disc and fuse the adjacent vertebrae. Typically, the fusion is facilitated by filling the intevertebral disk space with autograft bone graft (such as bone chips) which contain matrix molecules and living cells such as osteoblasts which facilitate fusion.

Figure 6:
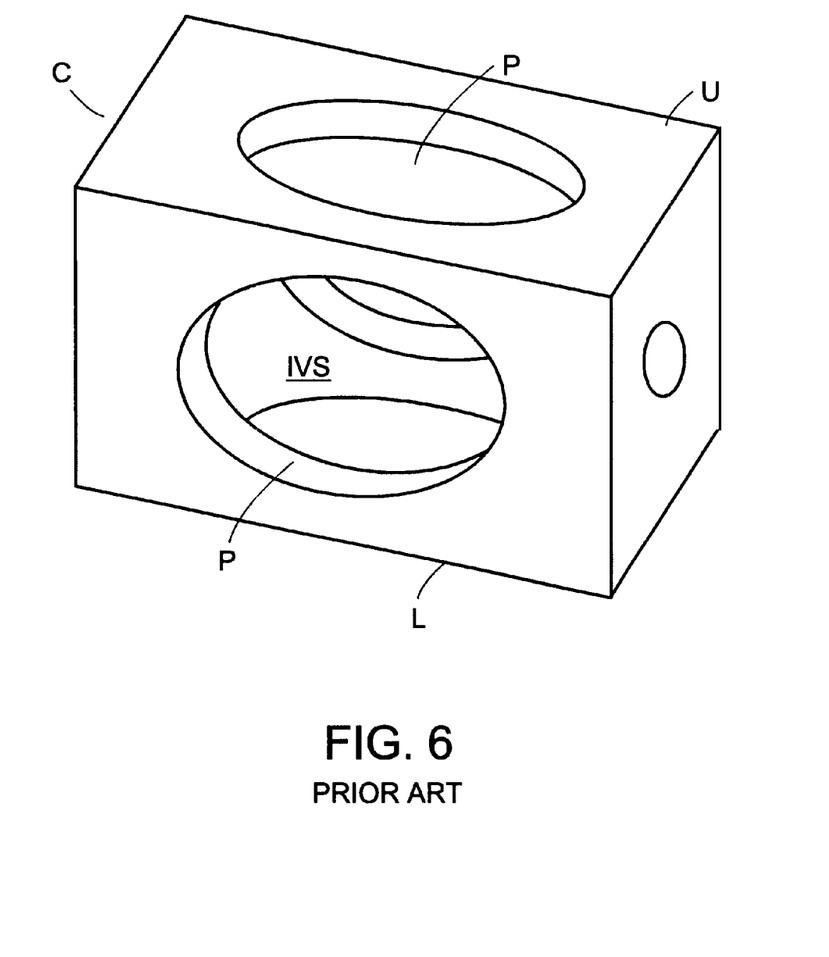
FIG. 6 is a perspective view of a conventional prior art support.

U.S. Pat. No. 4,743,256 ("Brantigan I") discloses an improved surgical method for eliminating spinal back pain caused by ruptured or degenerated vertebral discs. In this procedure, the problematic disk is first removed, and the disc space created between adjacent vertebrae is filled with rigid inert implants, or "cages". As shown in FIG. 6 herein, the upper U and lower L surfaces of these cages C have large transverse pores P which facilitate bone ingrowth, and these pores lead to an inner void space IVS which houses bone graft (not shown) which facilitates the desired fusion. These cage surfaces are also shaped to fit within prepared endplates of the vertebrae to integrate the implant with the vertebrae and to provide a permanent load-bearing strut for maintaining the disc space. Brantigan I teaches that these cages typically consist of a homogeneous nonresorbable material such as carbon-reinforced polymers such as polyether ether ketone (PEEK) or polyether ketone ether ketone ketone ("PEKEKK"). Although these cages have demonstrated an ability to facilitate fusion, a sufficient fusion is sometime not achieved between the bone chips housed within the cage and the vertebral endplates. In particular, achieving a complete fusion in the middle portion of the cage has been particularly problematic.

Accordingly, there is a need for an interbody fusion device which facilitates fusion in the middle portion of the cage.

Cages similar to those disclosed in Brantigan I have been made from a laminated material comprising a plurality of polyaryl ether ketone (PEAK) layers. However, each of the layers therein is non-resorbable.

Published PCT Application No. WO 99/08627 ("Gresser") discloses a fully bioresorbable interbody fusion device, as well as homogeneous composite devices containing at least 25% resorbable materials. Although the bioresorbable nature of this device is an attractive feature, if fusion of the endplates through the disk space does not occur, the eventual resorption of the disclosed device may lead to collapse of the disk space.

U.S. Pat. No. 5,702,449 ("McKay") discloses a spinal implant comprising a cage made of a porous biocompatible material reinforced by an outer sleeve made of a second material which is relatively stronger under the compressive load of the spine than the biocompatible material. Although McKay teaches that any porous biocompatible material may be used as the support, only porous ceramics are particularly described. This porous biocompatible material appears to be a substitute for bone graft material. Under normal physiologic loads, the outer sleeve is intended to bear most of the load without bending or fracture, and to protect the more brittle ceramic therein, while the porous bioceramic support carries a portion of the initial load and slowly transfers it to the newly formed bone. The porosity of the bioceramic material may be up to about 700 microns. In one embodiment, McKay teaches that the height of the sleeve is less than the height of the porous biocompatible material, so as to permit the porous biocompatible material to contact the vertebral endplates. McKay discloses a manufacturing process which involves heat shrinking the sleeve around the bioceramic material.

Although the implant disclosed by McKay has utility, it also carries with it a number of disadvantages. First, even with the protective sleeve, the bioceramic is still inherently brittle and subject to catastrophic flaws. Second, the manufacturing process is relatively complicated. Third, the requirement that the sleeve fit around the bioceramic limits the design possibilities of the system. Lastly, there is no provision for the use of bone graft material.

Some fusion cages have been introduced which contain bioresorbable layers upon their inner surfaces. These layers are used as carriers for therapeutic drugs and do not extend beyond the outer surface of the cage. Accordingly, they provide very little structural contribution to the cage. For example, An abstract by Kandziora et al., discloses coating a conventional fusion cage with bioresorbable materials. See Kandziora et al. "TGF-β and IGF-β Application by a Poly-(d,L)-Lactoide Coated Interbody Cage promotes Fusion In The Sheep Cervical Spine", Session 44, 47th Annual Meeting Orthopaedic Research Society, Feb. 25–28, 2001. These particular coatings comprised TGF-β and IGF-β disposed within a carrier matrix. The purpose of these coatings was to provide bone growth factors (TGF-β and IGF-β) to the fusion site. Although there is no specific disclosure of the coating thickness in the Kandziora et al. abstract, such coatings typically have a thickness of 1–20 μm, preferably 5–15 μm.

SUMMARY OF THE INVENTION

The present invention relates to an intervertebral bone fusion device having a structural bioresorbable layer disposed upon the outer surface of a non-resorbable support. As the bioresorbable structural layer resorbs over time, the load upon the bone graft housed within the non-resorbable support increases. This invention provides the user with an interbody fusion device which offers many advantages not offered by the conventional technology.

Figure 7:
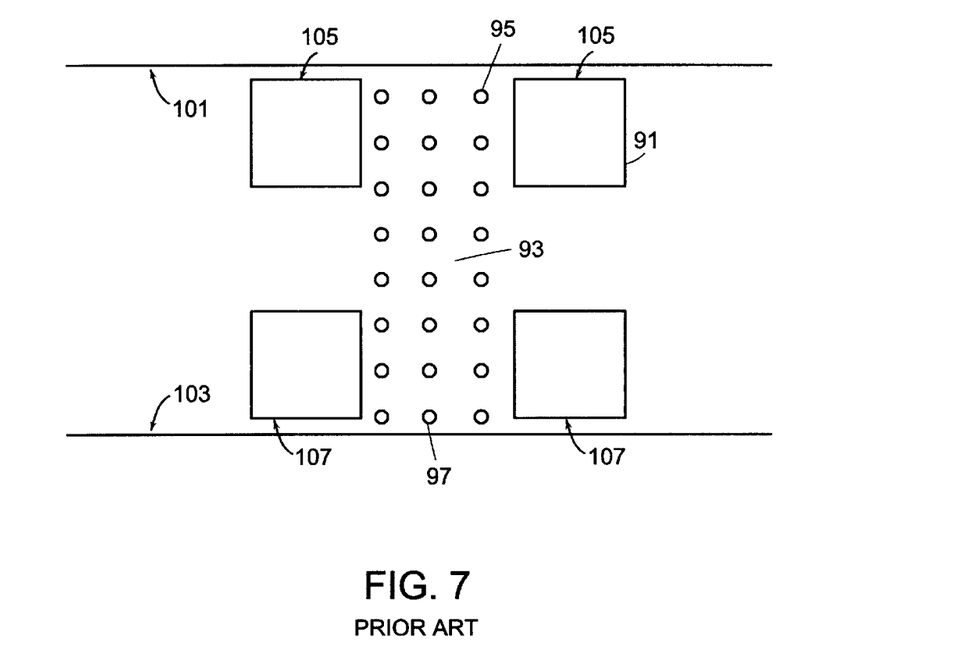
FIG. 7 is a cross-sectional view of a conventional prior art support filled with bone graft at the time of its insertion into an intervertebral disc space.

In general, the rate at which a bone graft remodels into bone is determined in part by the loading upon that graft. In particular, the higher the loading upon the graft, the faster the graft remodels. Therefore, higher loadings of bone graft are normally desirable. Now referring to cross-sectional FIG. 7 depicting a conventional fusion site, when a conventional cage 91 filled with bone graft 93 is placed within the disc space, the bone graft is loaded by virtue of the upper 95 and lower 97 surfaces of the bone graft respectively contacting the upper 101 and lower 103 vertebral endplates.

However, the present inventors recognized that the vertebral endplates responsible for loading the graft contact not only the bone graft, but also the upper 105 and lower 107 surfaces of the cage 91 as well. Consequently, the loading upon the bone graft plug by the endplates is limited by virtue of this shared-contact condition.

Accordingly, the present inventors set out to construct a device wherein the loading produced by the vertebral endplates would not always be shared between the bone graft and the upper 105 and lower 107 surfaces of the cage, but rather would eventually be directed solely to the bone graft.

Preferably, the present invention relates to the disposition of a bioresorbable structural layer upon at least one of the upper or lower surfaces of a support in the form of a cage. The addition of the bioresorbable layer to the upper and/or lower surfaces of the cage creates a reservoir for additional bone graft extending from the upper or lower opening in the cage and allows the bone graft plug to be built to a height greater than the cage. Upon resorption of the bioresorbable layer, only the taller bone graft contacts the endplates. Accordingly, the entire load of the endplates is no longer shared between the bone graft and the cage, but is now accepted only by the bone graft. This increased loading promotes fusion.

Moreover, if the desired interbody fusion does not occur, the non-resorbed cage material remains in place in the disk space and functions as a normal cage, thereby preventing collapse of the disk space. Accordingly, the device of the present invention possesses the advantages of the conventional technologies but with enhanced osteogenic potential in its middle portion and without the risk of disk space collapse.

Figure 1A:
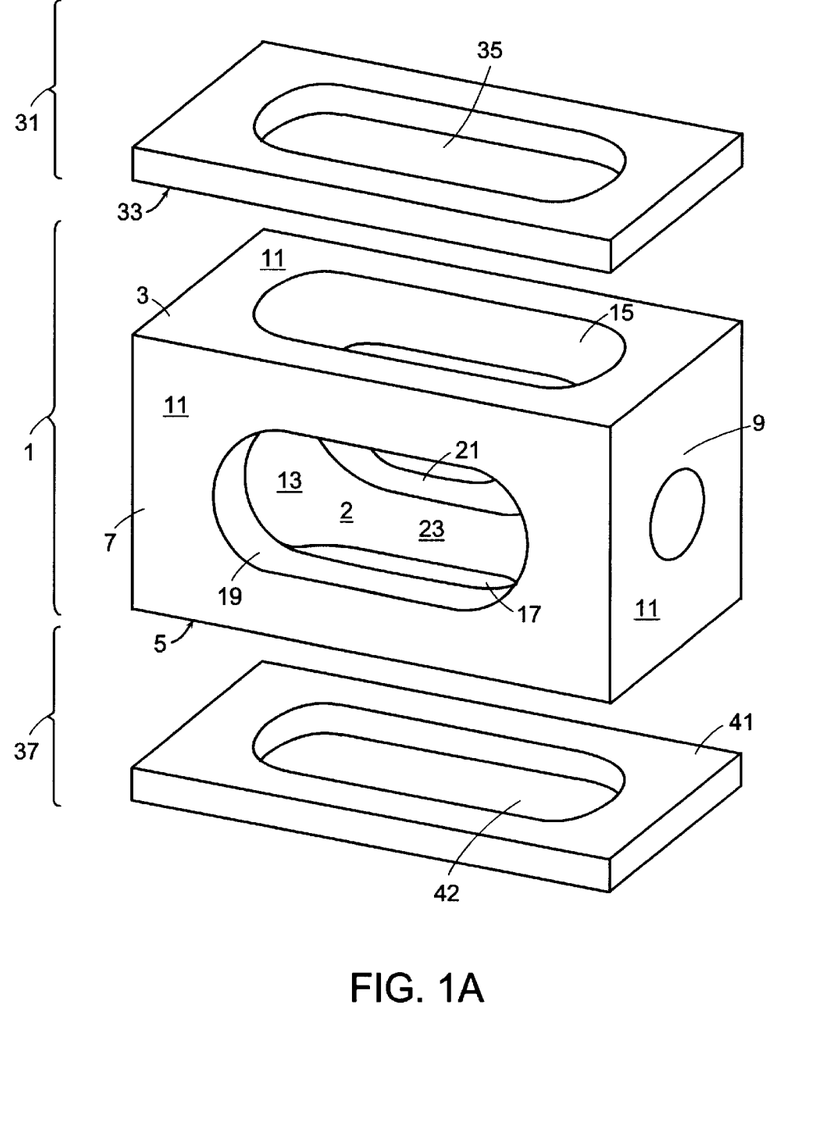
FIG. 1a is an exploded view of the device of the present invention.

Therefore, now referring to FIG. 1a, and in accordance with the present invention, there is provided an interbody fusion device comprising:

a) a non-resorbable support 1 having an outer surface 11, the support having an osteoconductive pore 2 passing therethrough and opening onto at least two openings 15,17 on the outer surface 11, and b) a first bioresorbable layer 31 disposed upon the outer surface 11 of the support, wherein the bioresorbable layer has a thickness TH of at least 100 μm.

Also in accordance with the present invention, there is provided an interbody fusion device comprising:

a) a non-resorbable support having an outer surface, the support having an osteoconductive pore passing therethrough and opening onto at least two openings on the outer surface, and b) a first bioresorbable layer comprising a polymer, the layer contacting the support and extending beyond the outer surface of the support, wherein the first bioresorbable layer has a thickness TH of at least 100 μm.

c)

Also in accordance with the present invention, there is provided an interbody fusion device comprising:

a) a non-resorbable support having an outer surface, the support having an osteoconductive pore passing therethrough and opening onto at least two openings on the outer surface, the pore defining an inner surface of the support, and b) a first bioresorbable layer contacting the inner surface of the support and extending beyond the outer surface of the support, wherein the contact of the bioresorbable layer upon the inner surface does not occlude at least two of the at least two openings at the outer surface, and wherein the first bioresorbable layer has a thickness TH of at least 100 μm.

DESCRIPTION OF THE FIGURES

FIG. 5b is a perspective view of the bioresorbable layer suitable for use with the support of FIG. 5a.

DETAILED DESCRIPTION OF THE INVENTION

For the purposes of the present invention, a "non-resorbable material" loses no more than 50% of its compressive strength after 24 months of implantation. "Bioresorbable" means that the material loses at least 50% of its compressive strength within 24 months of implantation.

Now referring to FIG. 1a, an exploded view of a preferred embodiment of the present invention, there is provided a non-resorbable support 1 having an upper contact surface 3, and a lower contact surface 5, these surfaces being connected by side surfaces 7, 9, each side surface forming a portion of the outer surface 11. Osteoconductive pore 2 passes completely through the support 1 from lower surface 5 to upper contact surface 3, and opens onto upper and lower openings 15, 17 formed in the upper 3 and lower 5 contact surfaces. Osteoconductive pore 2 forms a void 23 within the support and defines an inner surface 13, and opens onto side surface openings 19, 21 formed in side surfaces 7,9. Void section 23 is suitable for housing a bone growth material such as bone chips (not shown). In this case, the non-resorbable support 1 has a cage shape.

In addition, disposed upon the upper surface 3 of the support 1 is a first bioresorbable layer 31. This layer comprises a lower surface 33 which directly contacts the upper surface 3 of the support. Bioresorbable layer 31 also has a transverse hole 35 vertically disposed therethrough which opens onto upper opening 15 of the support. Likewise, a second bioresorbable layer 37 is disposed beneath the support and has an upper surface 41 which directly contacts the lower surface 5 of the support. Second bioresorbable layer 37 has a transverse hole 42 vertically disposed therethrough which opens onto lower opening 17 of the support.

Figure 1B:
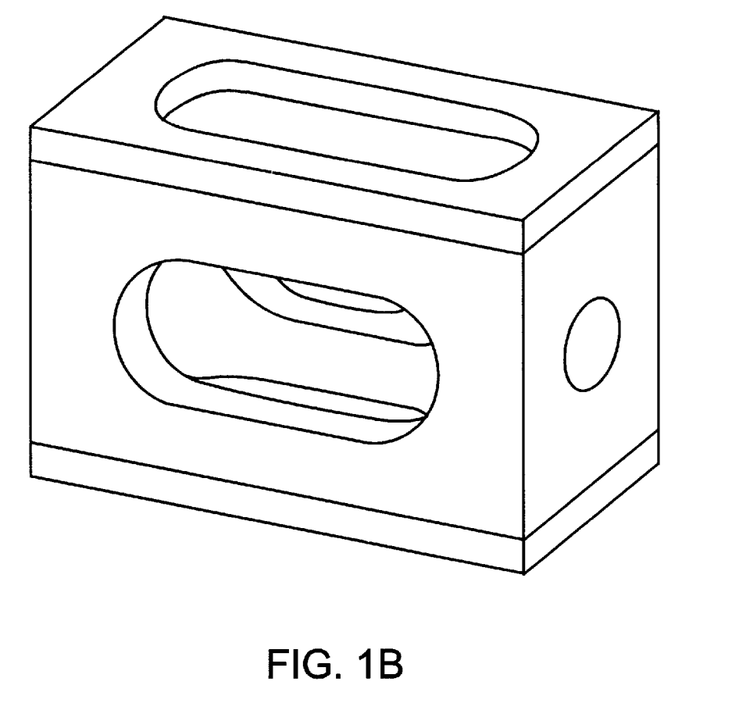
FIG. 1b is a perspective of a device of the present invention.

FIG. 1b presents a perspective view of the manufactured device represented by FIG. 1a. In this embodiment as shown in FIG. 1b, the a real ratio of the upper surface of the support to the upper surface of the bioresorbable layer is about 1:1.

Figure 1C:
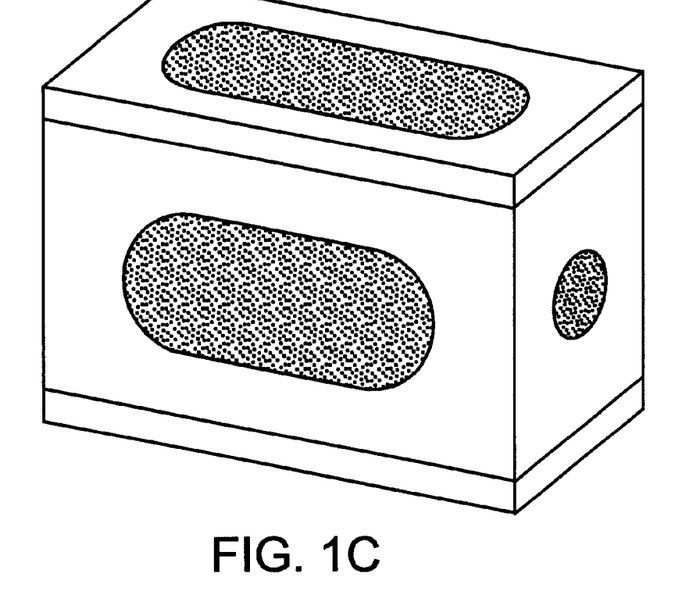
FIG. 1c is a perspective view of the device of the present invention filled with bone graft.
Figure 1D:
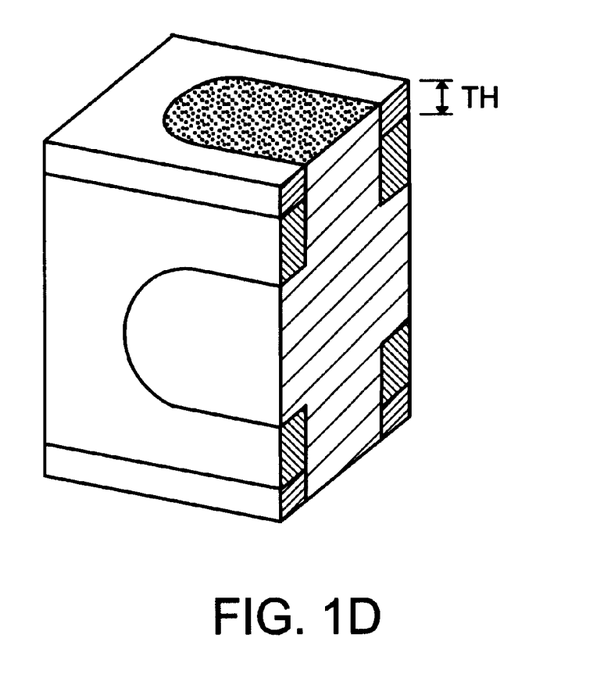
FIG. 1d is a perspective view of a cross-section of the implant of FIG. 1c.

FIG. 1c presents a perspective view of the device of FIG. 1b further loaded with bone graft material to form an implant. This bone graft material may include any number of materials known in the art, including autograft, allograft and synthetic ceramics. It may be used in any conventional form, such as in the form of chips, a powder or a gel. For examples of bone graft materials, see Thomas Bauer et al., entitled "Bone Graft Materials", *Clin. Orth. Rel. Res.* 371, pp. 10–27, 2000. FIG. 1d is a perspective view of a lateral cross-section of the device of FIG. 1c.

Figure 2A:
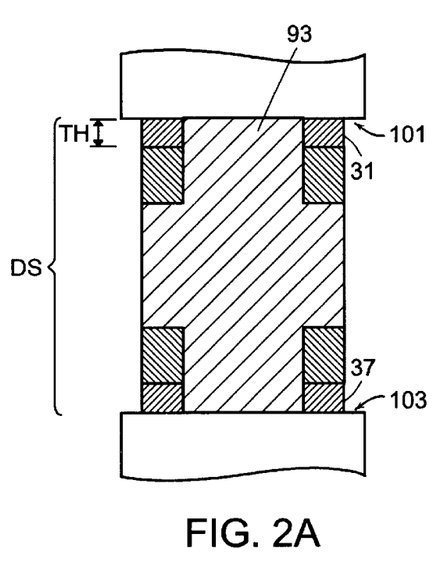
FIG. 2a is a cross-sectional view of the device of the present invention filled with bone graft at the time of its insertion into an intervertebral disc space.
Figure 2B:
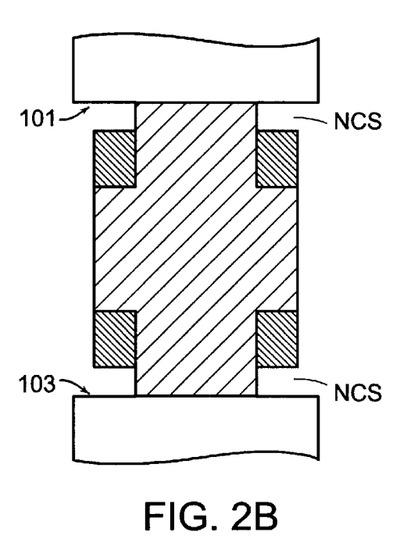
FIG. 2b is a cross sectional view of FIG. 2a after the bioresorbable layer has bioresorbed.

Now referring to FIG. 2a, when the inventive device of FIG. 1b is filled with bone graft 93 (as shown in FIG. 1c) and initially placed into the disc space DS, both the bone graft plug 93 and the bioresorbable layers 31,37 each contact the endplates 101,103, and so the loading upon the bone graft plug by the endplates is limited by virtue of its shared contact situation. However, as shown in FIG. 2b, as the bioresorbable layers resorb (over, for example, 6 months), the load is gradually transferred to the bone graft. Eventually, the complete resorption of the bioresorbable layer leaves a non-contact space NCS between the support and the endplates, and only the taller bone graft plug 93 remains in contact the vertebral plates 101, 103. Consequently, the bone graft no longer shares the endplate load with the support contact surface. Rather, the bone graft now accepts the entire load from the endplates. This increased loading of the bone graft should facilitate fusion in the problematic mid-portions of the support.

Although FIGS. 1b, 2a and 2b disclose bioresorbable layers upon both the upper and lower surface of the supports, the advantage of directing the loading to bone graft can also be realized by providing only one of the upper or lower surfaces of the support with a bioresorbable layer. When only a single bioresorbable layer is used, upon loading, the rate of load transfer to the bone graft is reduced by one-half.

Figure 2C:
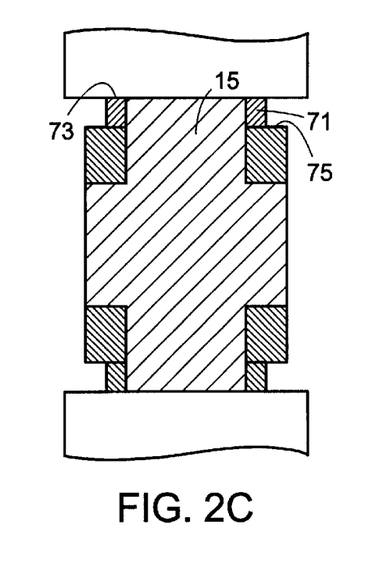
FIG. 2c is a cross-sectional view of a device of the present invention placed within a disk space, in which the bioresorbable layer forms a collar about the upper opening of the support.

In some embodiments, as in FIG. 2c, the horizontally disposed bioresorbable layer has a ring shape whereby it forms a collar 71 around upper opening 15. Since this collar has a reduced contact area, this embodiment provides a greater initial loading upon the bone graft plug than the embodiments in which the entire upper or lower surface of the support is covered by the bioresorbable layer. Therefore, fusion is enhanced at an earlier stage. Preferably, the collar 71 has a width such that the areal ratio of the collar upper surface 73 to the support upper surface 75 is between 50% and 95%. Within this range, the collar is sufficiently strong to support the endplates loading and yet sufficiently narrow to provide increased loading.

The advantages of the device of FIG. 2c (over that shown in FIG. 1b) include a reduction in the stiffness of the overall device (since the layer does not span the entire upper surface of the support) and a higher rate of absorption (since the load on this layer is higher. However, this device of FIG. 2c is also somewhat less stable than that of FIG. 1b.

Therefore, in some embodiments, the first opening has a perimeter, wherein the first bioresorbable layer is disposed upon a portion of the upper contact surface and is located substantially adjacent the perimeter of the first opening in the upper contact surface.

In some embodiments, the bioresorbable layer is disposed vertically upon the support. Now referring to FIG. 3a, a bioresorbable layer 41 is vertically disposed upon vertical inner surfaces 43–46 of the support. However, upper portions 47,48 extend beyond the upper surface 3 of the support, while lower portions 49, 50 extend beyond the lower surface 5 of the support, thereby allowing the construction of a taller bone graft plug therewithin. At implantation, the endplate load is shared by the bone graft plug and by the upper surfaces of the bioresorbable layers. However, as in FIG. 2c, the surface area of the bioresorbable layer which contacts the endplates is less than the surface area of the upper surface of the support, and so an increased loading by the bone graft is enjoyed from the outset. Moreover, since the diameter $D_{BGP}$ of the bone graft plug is limited to a diameter which is less than that of the osteoconductive pores $D_{OP}$, the eventual loading of the bone graft plug of FIG. 3a will be even greater than the loading experienced by the bone graft plug of FIG. 2a. When layer 41 fully resorbs, only the bone graft plug is loaded.

Figure 3A:
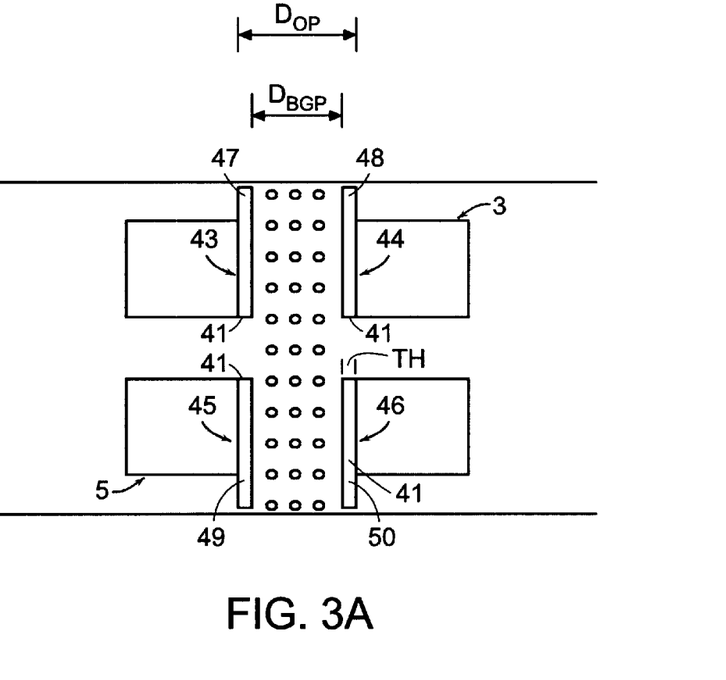
FIG. 3a is a cross-sectional view of the device of the present invention placed within a disk space, and in which the bioresorbable layer is vertically disposed upon the inner surfaces of the support.

The advantages of the device of FIG. 3a over that of FIG. 2c include a reduction in the stiffness of the overall device (since the layer is not supported by the support). However, this device of FIG. 3a is somewhat more susceptible to shear vertical forces than the device of FIG. 2c.

Figure 3B:
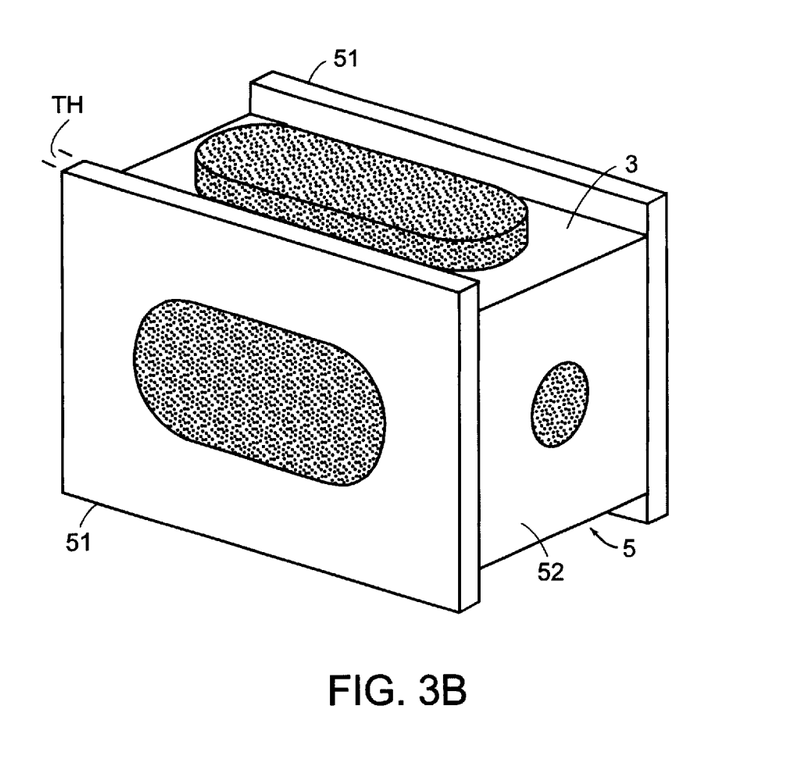
FIG. 3b is a perspective view of a device of the present invention filed with bone graft, and in which a pair of bioresorbable layers are disposed upon at least two side surfaces of the support.
Figure 3C:
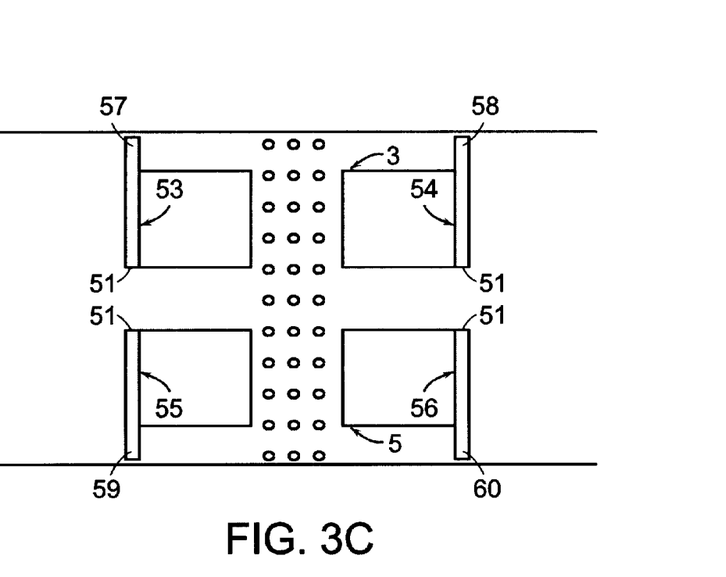
FIG. 3c is a cross-sectional view of the device of the present invention placed within a disk space, in which the bioresorbable layer is vertically disposed upon the outer surfaces of the support.

Likewise, and now referring to FIGS. 3b and 3c, bioresorbable layer 51 is vertically disposed upon outer surfaces 53–56 of support 52. The upper 57,58 and lower 59,60 portions of these layers extend beyond the horizontally disposed support upper 3 and lower 5 support surfaces, again allowing the construction of a taller bone graft plug. Now referring to FIG. 3c, at implantation, the endplate load is shared by the bone graft plug and by extreme portions 57–60 of the bioresorbable layer 51. When layer 51 resorbs, only the bone graft plug is loaded.

Although the eventual loading of the bone graft plug of this embodiment will not be as great as that provided by the device of FIG. 2a, this embodiment allows bone graft to be disposed all along the upper surface of the support, thereby enhancing osteogenesis. The advantages of the device of FIG. 3b include reduced stiffness (since the layer is not vertically supported by the support).

In some embodiments, the horizontal bioresorbable layer has at least one tooth extending away from the outer surface and shaped for grasping the endplates. In some preferred embodiments, as in FIG. 4a, teeth 61 are formed by providing a layer of uniform thickness upon a support having a toothed upper surface 63. In other embodiments, as in FIG. 4b, the teeth 65 are formed solely in the bioresorbable layer disposed upon a flat upper surface 67.

Figure 4A:
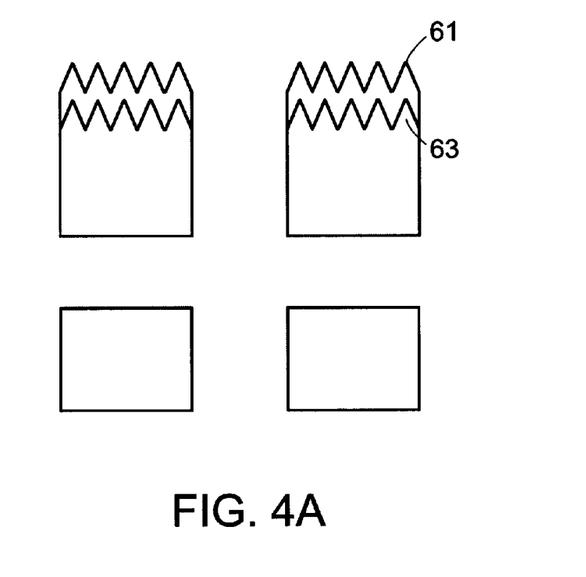
FIGS. 4a–c are cross sectional views of embodiments of the present invention in which the bioresorbable layer forms teeth.
Figure 4B:
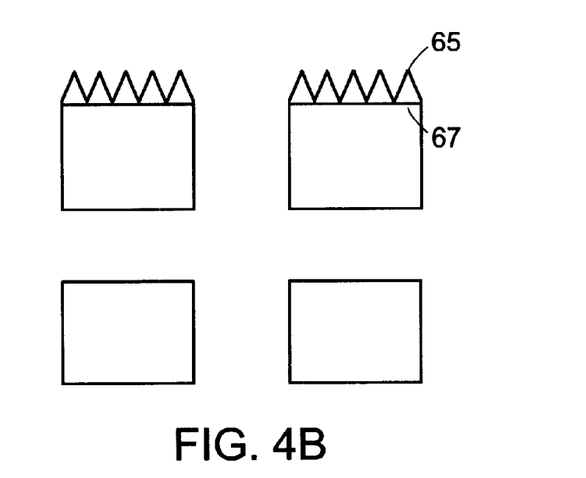

The advantages of the devices of FIGS. 4a and 4b include the ability of the teeth to grasp the endplates and higher rates of absorption (owing to the reduced surface area of and higher loading upon the teeth).

Therefore, in some embodiments, the contact surface upon which the first bioresorbable layer is disposed has a perimeter, and wherein the at least one tooth has a leading edge facing the perimeter of the contact surface upon which it is disposed.

Figure 4C:
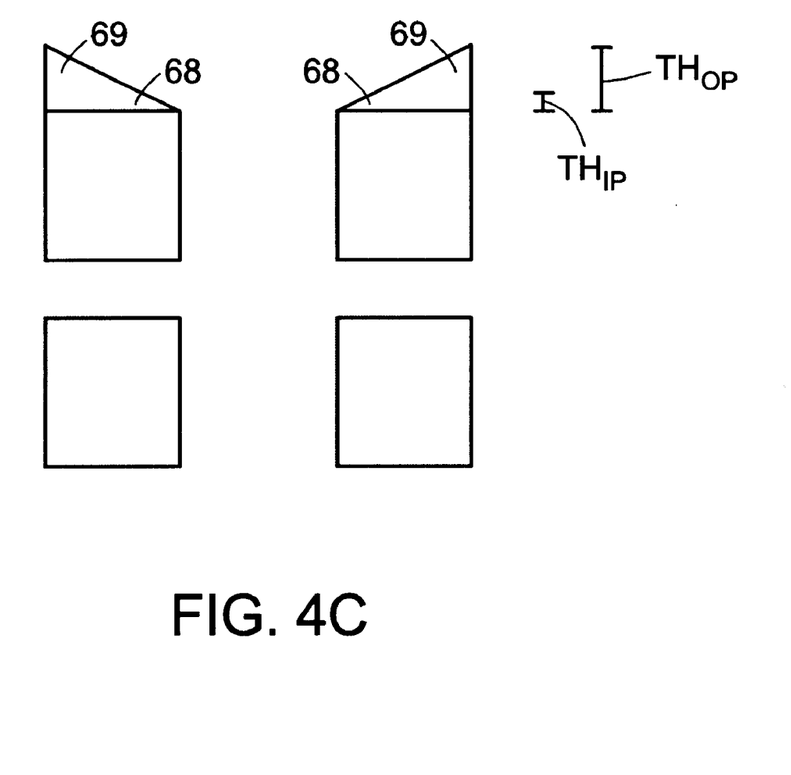
Figure 4D:
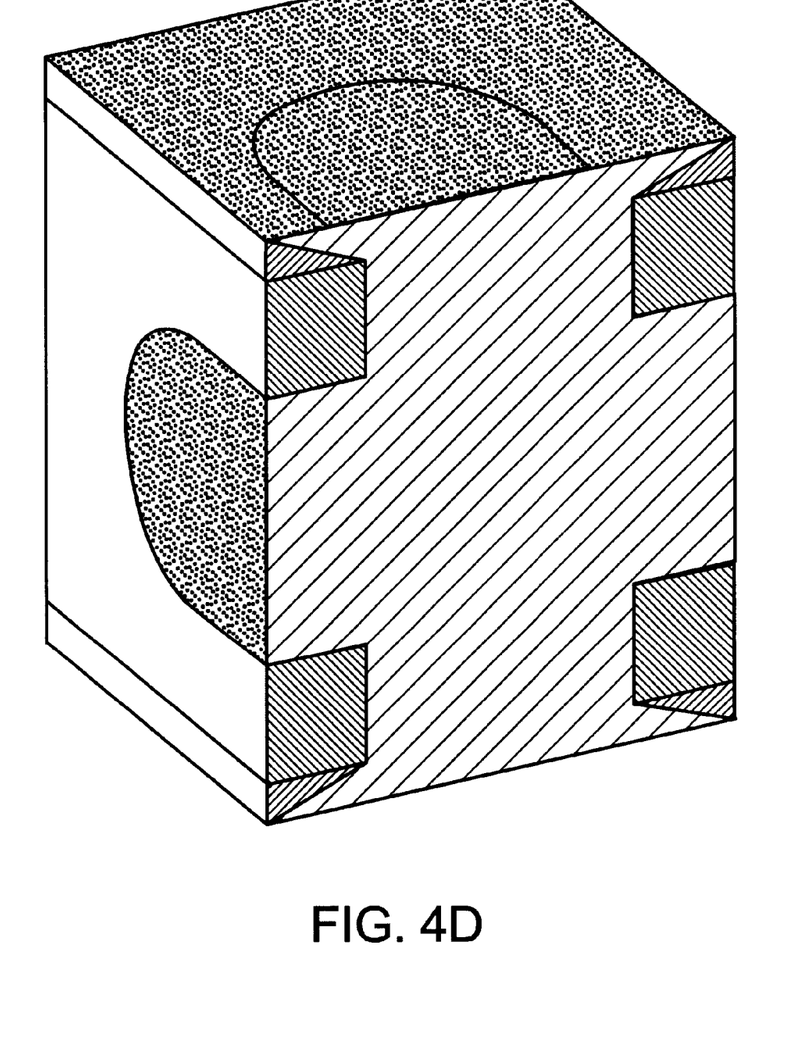
FIG. 4d is a perspective view of a cross-sectioned device of the present invention filled with bone graft, in which the bioresorbable layers form longitudinally extending teeth.

Now referring to FIG. 4c, in another embodiment, the thickness of the horizontally-disposed bioresorbable layer increases towards the periphery of the upper surface to form a pair of teeth. That is, the thickness $TH_{IP}$ of the inner portion 68 of the layer is less than the thickness $TH_{OP}$ of the outer portion 69 of the layer. This embodiment provides a stable grip upon the endplate which resists lateral movement. Since there is now resistance to lateral movement, the need to form a channel in the endplate (in order to minimize lateral movement of the conventional cage) may be obviated. When this layer is disposed upon a support whose upper surface has teeth configured to resist axial movement, the resulting device is stable against both axial and lateral movement. In addition, this device is easy to manufacture, has good stability and allows the use of more bone graft, as shown in FIG. 4d, due to the reservoir it forms above the upper surface of the support.

Therefore, in some embodiments, the upper contact surface has a perimeter, wherein the first bioresorbable layer is disposed upon a portion of the upper contact surface and is located substantially adjacent the perimeter of the upper contact surface.

In some embodiments, there is provided an interbody fuision device having a reservoir comprising:
  a) a non-resorbable support having an outer surface and an upper surface, the support having an osteoconductive pore passing therethrough and opening onto at least two openings on the outer surface, and
  b) at least one wall disposed upon the outer surface of the support and extending above the upper surface to form the reservoir upon the upper surface.

Preferably, the at least one opening comprises an upper opening which opens onto the upper surface and has a perimeter, and wherein the wall surrounds at least one-half of the perimeter of the opening, and is bioresorbable. Preferably, the wall substantially surrounds the perimeter of the upper opening, and is disposed upon the upper surface. Preferably, the support further comprises:
  c) a lower surface, and
  d) a side surface between the upper and lower surfaces, and
wherein the wall is disposed upon the side surface.

The osteoconductive pore 2 should have a diameter that allows for bony ingrowth leading to fusion of the intervertebral space. Preferably, the osteoconductive pore is at least 100 um in diameter, more preferably more than 250 um in diameter. Most preferably, the osteoconductive pore is between 1 mm and 10 mm in diameter.

In some embodiments, the osteoconductive pore forms a void within the support, the void defining a void volume and an inner surface, wherein the outer surface of the support defines a support volume, wherein the void volume is at least 10–50% of the support volume.

The bioresorbable material must be sterile. Preferably, the bioresorbable material comprises a polymer, and more preferably at least 90 vol % of the bioresorbable material comprises a polymer. Polymers are advantageous over other bioresorbable materials because they are highly reproducible and have high toughness. When the polymer is tough, the danger of its failing by brittle fracture is significantly reduced. In that case, there is no need for the implant design to require that the stronger support material put the bioresorbable material into compression (as McKay requires) and so many new designs of resorbable/non-resorbable composites are possible.

The most preferred bioresorbable material is selected from the group consisting of poly(lactic acid) ("PLA") and poly(glycolic acid)("PGA"), and copolymers thereof These materials are preferred because they possess suitable strength and biocompatibility, display desirable resorption profiles, and have a long history of safe in vivo use. In general, PLA is a desirable because it typically has a resorption time exceeding 12 months, whereas PGA resorbs fairly quickly (having a resorption time of less than 12 months). However, PLA can require many years to completely resorb, and so is more likely to produce foreign-body reactions. Therefore, more preferably, the material is a PLA/PGA copolymer, more preferably the copolymer comprises between 80 wt % and 99 wt % lactic acid (as PLA), and between 1 wt % and 20 wt % glycolic acid (as PGA). Copolymers within these ranges provide the proper balance between the strength and the resorption time.

Other synthetic organic materials include, caprolactone; hydroxybutyrate; Idioxanone; oerthoesters; oerthocarbonates; and aminocarbonates. Other preferred bioresorbable materials include natural materials such as chitosan, collagen, cellulose, ceramics, fibrin, hyaluronic acid; fibronectin, and mixtures thereof In some embodiments, the bioresorbable layer has a resorption time of between 3 months and 48 months.

The non-resorbable support is sterile and can be made of any material which does not resorb and which is sufficiently strong to prevent collapse of the disk space in the event of non-fusion. The support component of the present invention may be made from any non-resorbable material appropriate for human surgical implantation, including but not limited to all surgically appropriate metals including titanium, titanium alloy, chrome alloys and stainless steel, and non-resorbable non-metallic materials such as carbon fiber materials, resins, plastics and ceramics. Preferred materials include polyesters, (particularly aromatic esters such as polyalkylene terephthalates, polyamides; polyalkenes; poly(vinyl fluoride); PTFE; carbon fibres; silk; and glass, and mixtures thereof Preferably, the material used as the non-resorbable support is a PEAK material, and more preferably is selected from the group consisting of PEEK, PEK, PEKK and PEKEKK.

The purpose of the non-resorbable support is to act as a scaffold for the bioresorbable support in the early stages of fusion and to remain in place in the event fusion does not occur. Preferred non-resorbable supports include cages (such as that shown in FIG. 3 of Weiner, Spine, 23(5) 634–640, 1998.), rings (such as that shown in FIG. 2 of Weiner), sleeves (such as that shown in McKay) and mesh (such as that shown in FIG. 1 of U.S. Pat. No. 4,820,305 ("Harms"). Preferably, the support has a design disclosed in any of U.S. Pat. Nos. 5,425,772; 5,192,327; 4,878,915; 4,834,757 and 4,743,256 (Brantigan), the specifications of which are incorporated by reference.

The non-resorbable support can have any shape suitable for indefinitely supporting the disk space. Preferably, the non-resorbable support has a shape selected from a horizontal threaded cylinder, a vertical ring, and an open box cage. Preferably, the non-resorbable support has a cage design.

The thickness of the bioresorbable layer is measured as the depth of the material (i.e., the shortest distance between the outer surface of the bioresorbable layer and the outer surface of the support). For example, the thicknesses TH of selected bioresorbable layers are shown in FIGS. 1d, 2a, 3a and 4c. In order to produce an appreciable amount of the desired load-transfer effect, at least a portion of the thickness of the bioresorbable layer needs to be at least 100 μm, preferably at least 200 μm, more preferably at least 500 μm, still more preferably between 1 mm and 8 mm, most preferably between 2 mm and 4 mm. Thicknesses greater than 200 μm are more desirable than 100 um thicknesses because the greater thickness helps insure that irregularities in the adjacent vertebral endplate surface or inhomogeneous bone graft packing do not result in direct contact between the endplate and the support. Thicknesses of at least 500 μm, at least 1 mm and at least 2 mm successively provide even greater insurance against these concerns. Also preferably, the thickness of the bioresorbable layer should not exceed 8 mm, since devices having layers exceeding this thickness may cause the disc space to suffer from too great a collapse in the event of device failure. In some embodiments, the resorbable material comprises between 5% and 50% of the overall thickness of the device.

Figure 5A:
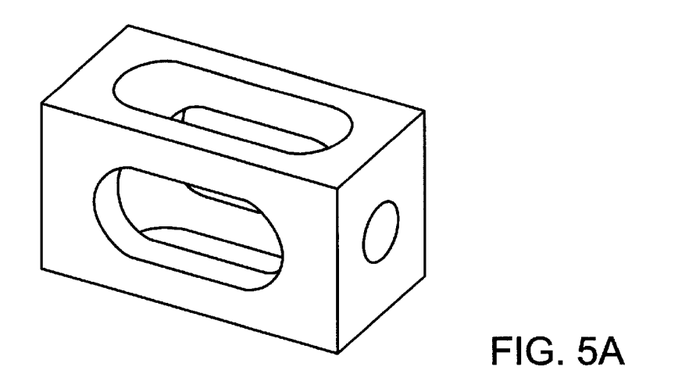
FIG. 5a is a perspective view of a non-resorbable support of the present invention.
Figure 5B:
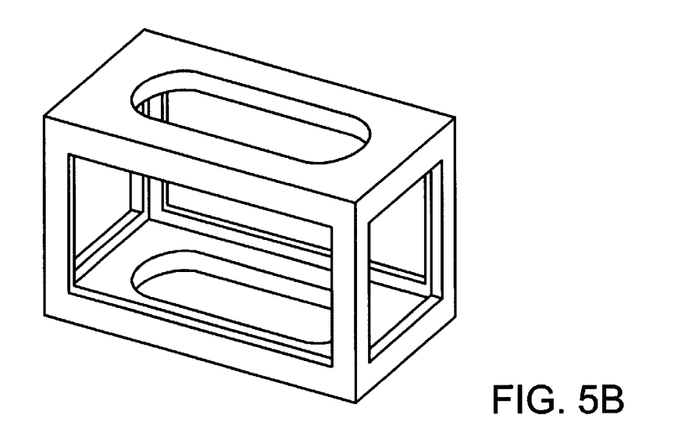
Figure 5C:
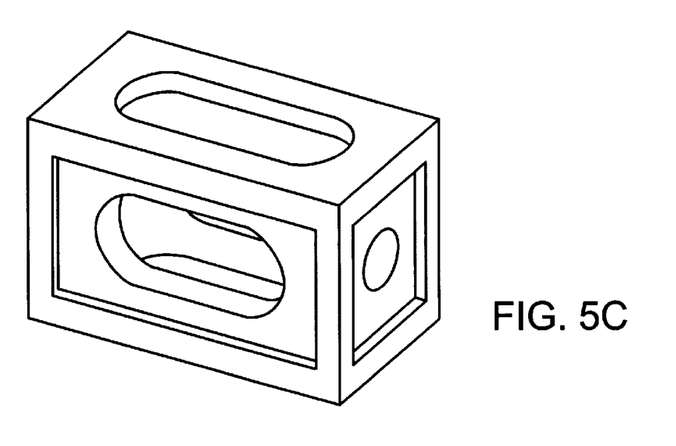
FIG. 5c is a perspective view of the non-resorbable support of FIG. 5a covered in the bioresorbable layer of FIG. 5b.
Figure 5D:
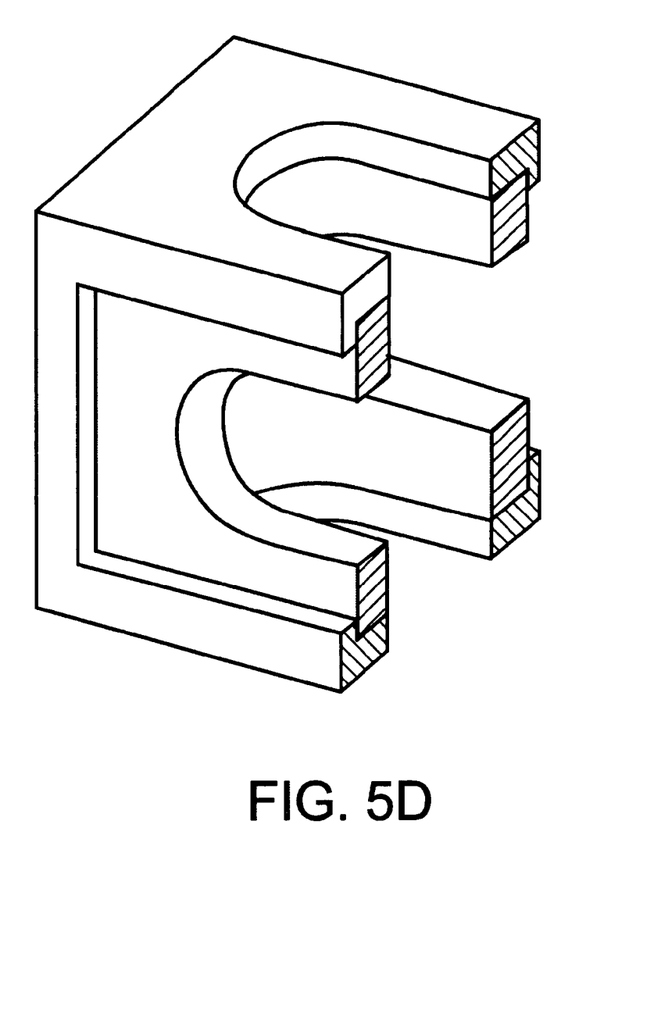
FIG. 5d is a cross-sectioned perspective view of the device of FIG. 5c.

In some embodiments, the device is made in a piecemeal fashion, that is, the support is fully manufactured and then the bioresorbable layer is disposed thereon. In some cases, now referring to FIG. 5a, the support is first manufactured by conventional molding and/or machining processes. Next, the support is placed in an oversized mold having the shape of the final device and held in place. Lastly, now referring to FIG. 5b, resorbable material is injected into the mold over the non-resorbable support, thereby forming the desired layer over the support. The resulting device is shown in FIG. 5c. A perspective view of a cross-section of FIG. 5c is shown in FIG. 5d.

In some embodiments, the surface of the support maybe textured in order to promote adhesion of the bioresorbable layer thereon.

If use of the device of the present invention results in a successful fusion, then the device should be seen on an x-ray as being suspended within the newly formed bone, and should not be contacting the endplates. In contrast, if bony fusion does not occur, then the device will likely subside into the endplates. Therefore, in addition to its utility as an improved fusion device, the device of the present invention also allows the surgeon to analyze the efficacy of the fusion by simply determining whether the device is suspended within the newly formed bone.

We claim:

1. An interbody fusion device comprising:
   a) a non-resorbable support having an outer surface, the support having an osteoconductive pore passing therethrough and opening onto at least two openings on the outer surface, and
   b) a first bioresorbable layer disposed upon the outer surface of the support,
wherein the first bioresorbable layer has a thickness TH of at least 100 μm.

2. The device of claim 1 wherein the outer surface comprises upper and lower contact surfaces, and wherein the first bioresorbable layer is disposed upon at least one of the contact surfaces.

3. The device of claim 2 wherein the first bioresabable layer is disposed upon the upper contact surface.

4. The device of claim 2 wherein the first bioresorbable layer is disposed upon the lower contact surface.

5. The device of claim 2 comprising first and second openings, wherein the first opening is formed in the upper contact surface and wherein the second opening is formed in the lower contact surface.

6. The device of claim 5 wherein the first opening has a perimeter, and wherein the first bioresorbable layer is disposed upon a portion of the upper contact surface and is located substantially adjacent the perimeter of the first opening in the upper contact surface.

7. The device of claim 5 wherein the upper contact surface has a perimeter, and wherein the first bioresorbable layer is disposed upon a portion of the upper contact surface and is located substantially adjacent the perimeter of the upper contact surface.

8. The device of claim 5 wherein the thickness of the first bioresorbable layer is at least 200 μm.

9. The device of claim 5 wherein the thickness of the first bioresorbable layer is at least 500 μm.

10. The device of claim 5 wherein the thickness of the first bioresorbable layer is betweem 1 mm and 8 mm.

11. The device of claim 5 wherein the thickness of the first bioresorbable layer is between 1 mm and 8 mm.

12. The device of claim 5 wherein the thickness of the first bioresorbable layer is between 2 mm and 4 mm.

13. The device of claim 5 further comprising:
   c) a second bioresorbable layer,
wherein the first bioresorbable layer is disposed upon the upper contact surface, and the second bioresorbable layer is disposed upon the lower contact surface.

14. The device of claim 1 wherein the outer surface comprises upper and lower contact surfaces, and at least a first side surface therebetween, and the first bioresorbable layer is disposed upon the first side surface and extends beyond at least one of the upper and lower contact surfaces.

15. The device of claim 14 further comprising:
   c) a second bioresorbable layer,
wherein the outer surface further comprises a second side surface between the upper and lower contact surfaces, and the second bioresorbable layer is disposed upon the second side surface and extends beyond at least one of the upper and lower contact surfaces.

16. The device of claim 15 wherein each bioresorbable layer extends beyond each contact surface.

17. The device of claim 1 wherein the osteoconductive pore forms a void within the support, the void defining a void volume and an inner surface, wherein the outer surface of the support defines a support volume, wherein the void volume is at least 10–50% of the support volume.

18. The device of claim 17 wherein the support is a cage.

19. The device of claim 1 wherein the first bioresorbable layer forms at least one tooth extending away from the outer surface upon which the first bioresorbable layer is disposed.

20. The device of claim 19 wherein the outer surface comprises upper and lower contact surfaces, and wherein first bioresorbable layer is disposed upon at least one of the contact surfaces.

21. The device of claim 20 wherein the contact surface upon which the first bioresorbable layer is dispose has a perimeter, and wherein the at least one tooth has a leading edge facing the perimeter of the contact surface upon which it is disposed.

22. The device of claim 1 wherein the bioresorbable layer has a resorption time of between 3 months and 48 months.

23. The device of claim 1 wherein the bioresorbable layer comprises a polymer.

24. The device of claim 23 wherein the polymer is selected from the group consisting of PLA, PGA, and copolymers thereof.

25. An interbody fusion device comprising:
   a) a non-resorbable support having an outer surface, the support having an osteoconductive pore passing therethrough and opening onto at least two openings on the outer surface, and a first bioresorbable layer comprising a polymer, the layer contacting the support and extending beyond the outer surface of the support, wherein the first bioresorbable layer has a thickness TH of at least 100 μm.

26. The device of claim 25 wherein the osteoconductive pore defines an inner surface of the support, and the first bioresorbable layer contacts the inner surface of the support.

27. The device of claim 26 wherein the outer surface comprises upper and lower contact surfaces, and wherein the first bioresorbable layer extends beyond at least one of the upper and lower contact surfaces.

28. The device of claim 27 wherein the first bioresorbable layer extends beyond each of the upper and lower contact surfaces.

29. The device of claim 28 wherein the first opening is formed in the upper contact surface and wherein the second opening is formed in the lower contact surface.

30. The device of claim 29 wherein the first bioresorbable layer forms at least one tooth extending away from the outer surface upon which the first bioresorbable layer is disposed.

31. An interbody fusion device comprising:
a) a non-resorbable support having an outer surface, the support having an osteoconductive pore passing therethrough and opening onto at least two openings on the outer surface, the pore defining an inner surface of the support, and
b) a first bioresorbable layer contacting the inner surface of the support and extending beyond the outer surface of the support,
wherein the contact of the bioresorbable layer upon the inner surface does not occlude at least two of the at least two openings at the outer surface, and wherein the first bioresorbable layer has a thickness TH of at least 100 μm.

32. The device of claim 31 wherein the outer surface comprises upper and lower contact surfaces, wherein the first bioresorbable layer extends beyond at least one of the upper and lower contact surfaces.

33. The device of claim 32 wherein the first bioresorbable layer extends beyond each of the upper and lower contact surfaces.

34. The device of claim 33 wherein the first opening is formed in the upper contact surface and wherein the second opening is formed in the lower contact surface, and wherein the contact of the bioresorbable layer upon the inner surface does not occlude the first and second openings at the outer surface.

35. The device of claim 34 wherein the first bioresorbable layer forms at least one tooth extending away from the contact surfaces.

36. An interbody fusion device comprising:
a) a non-resorbable support having an outer surface and an upper surface, the support having an osteoconductive pore passing therethrough and opening onto at least two openings on the outer surface, and
b) at least one wall disposed upon the outer surface of the support and extending above the upper surface to form a reservoir upon the upper surface,
wherein the first bioresorbable layer has a thickness TH of at least 100 μm.

37. The device of claim 33 wherein the at least one opening comprises an upper opening which opens onto the upper surface and has a perimeter, and wherein the wall surrounds at least one-half of the perimeter of the opening.

38. The device of claim 37 wherein the wall substantially surrounds the perimeter of the upper opening.

39. The device of claim 37 wherein the wall is disposed upon the upper surface.

40. The device of claim 37 wherein the support further comprises:
c) a lower surface, and
d) a side surface between the upper and lower surfaces, and
wherein the wall is disposed upon the side surface.

41. The device of claim 37 wherein the wall is bioresorbable.

* * * * *